(12) United States Patent
Dextradeur

(10) Patent No.: US 9,901,707 B2
(45) Date of Patent: Feb. 27, 2018

(54) CATHETER CURVATURE BRACES AND METHODS OF USING SAME

(75) Inventor: Alan Dextradeur, Franklin, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 764 days.

(21) Appl. No.: 13/478,487

(22) Filed: May 23, 2012

(65) Prior Publication Data

US 2013/0317410 A1    Nov. 28, 2013

(51) Int. Cl.
| | | |
|---|---|---|
| A61M 1/00 | (2006.01) | |
| A61M 25/00 | (2006.01) | |
| A61M 27/00 | (2006.01) | |
| A61M 25/01 | (2006.01) | |
| A61M 25/04 | (2006.01) | |

(52) U.S. Cl.
CPC ...... A61M 25/0041 (2013.01); A61M 27/006 (2013.01); A61M 25/0082 (2013.01); A61M 25/0102 (2013.01); A61M 25/04 (2013.01)

(58) Field of Classification Search
USPC ................................................ 604/524, 528
See application file for complete search history.

(56) References Cited

U.S. PATENT DOCUMENTS

| | | | | |
|---|---|---|---|---|
| 3,608,555 A | * | 9/1971 | Greyson | .................. A61L 29/18 |
| | | | | 138/118 |
| 3,867,945 A | | 2/1975 | Long | |
| 3,885,561 A | * | 5/1975 | Cami | .................. A61M 25/007 |
| | | | | 137/493 |
| 3,894,541 A | * | 7/1975 | El-Shafei | .............. A61M 1/008 |
| | | | | 604/10 |

(Continued)

FOREIGN PATENT DOCUMENTS

| | | |
|---|---|---|
| JP | 2-149253 U | 12/1990 |
| JP | 09-099088 A | 4/1997 |

(Continued)

OTHER PUBLICATIONS

Lind, C., et al; Ventricular Catheter Placement Accuracy in Non-Stereotactic Shunt Surgery for Hydrocephalus; Journal of Clinical Neuroscience; 2009; pp. 918-920; 16; Neurosurgical Society of Australasia.

(Continued)

*Primary Examiner* — Todd J Scherbel
*Assistant Examiner* — Guy K Townsend
(74) *Attorney, Agent, or Firm* — Troutman Sanders LLP

(57) ABSTRACT

A catheter curvature brace, catheter assembly and method for managing fluid in a patient, the brace being attachable to a distal portion of a shaft of a catheter and having an elongated frame with a distal end and a proximal end. The frame is formed with at least one curve in a relaxed curved configuration. At least two coupling elements are connected to the frame, each coupling element configured to engage an outer surface of the catheter. At least the frame is formed of an elastic, biocompatible material capable of being straightened by a force and then returning to the relaxed curved configuration after the force is removed, thereby bending the catheter to substantially conform to the relaxed curved configuration.

7 Claims, 3 Drawing Sheets

(56) References Cited

U.S. PATENT DOCUMENTS

| | | | |
|---|---|---|---|
| 4,382,445 A * | 5/1983 | Sommers | A61M 25/0075 604/8 |
| 4,613,324 A * | 9/1986 | Ghajar | A61B 17/3403 604/264 |
| 4,632,668 A * | 12/1986 | Wilson, Jr. | A61M 27/006 604/540 |
| 4,655,745 A * | 4/1987 | Corbett | A61M 25/02 604/103.07 |
| 4,784,638 A * | 11/1988 | Ghajar | A61M 25/007 138/103 |
| 4,821,716 A * | 4/1989 | Ghajar | A61B 17/1695 604/174 |
| 4,861,331 A * | 8/1989 | East | A61M 27/006 137/854 |
| 4,931,056 A * | 6/1990 | Ghajar | A61B 17/1695 604/174 |
| 5,180,387 A * | 1/1993 | Ghajar | A61M 25/001 604/266 |
| 5,190,528 A | 3/1993 | Fonger | |
| 5,382,238 A | 1/1995 | Abrahamson | |
| 5,405,316 A * | 4/1995 | Magram | A61M 27/006 604/175 |
| 5,688,237 A | 11/1997 | Rozga | |
| 5,738,666 A | 4/1998 | Watson | |
| 6,001,078 A | 12/1999 | Reekers | |
| 6,021,340 A | 2/2000 | Randolph | |
| 6,071,274 A * | 6/2000 | Thompson | A61B 18/1492 604/528 |
| 6,071,279 A * | 6/2000 | Whayne | A61B 18/1492 606/41 |
| 6,076,012 A * | 6/2000 | Swanson | A61B 18/1492 604/21 |
| 6,193,691 B1 * | 2/2001 | Beardsley | A61M 25/007 604/164.01 |
| 6,197,003 B1 | 3/2001 | Garrell et al. | |
| 6,231,563 B1 | 5/2001 | White | |
| 6,261,304 B1 | 7/2001 | Hall | |
| 6,330,473 B1 * | 12/2001 | Swanson | A61B 18/1492 604/21 |
| 6,332,880 B1 * | 12/2001 | Yang | A61M 25/0043 604/528 |
| 6,569,150 B2 | 5/2003 | Teague | |
| 6,875,192 B1 * | 4/2005 | Saul | A61M 27/006 604/264 |
| 7,115,134 B2 | 10/2006 | Chambers | |
| 7,144,363 B2 * | 12/2006 | Pai | A61B 17/00234 600/16 |
| 7,371,210 B2 * | 5/2008 | Brock | A61B 34/20 600/114 |
| 7,530,963 B2 * | 5/2009 | Albright | A61B 17/11 604/8 |
| 7,699,800 B2 * | 4/2010 | Dextradeur | A61M 25/0662 604/4.01 |
| 7,771,411 B2 * | 8/2010 | Smith | A61B 18/1492 604/523 |
| 7,867,219 B2 | 1/2011 | Chambers | |
| D672,064 S * | 12/2012 | Grandich | A61M 25/0021 D25/136 |
| 2002/0077595 A1 | 6/2002 | Hundertmark | |
| 2002/0087048 A1 * | 7/2002 | Brock | A61B 34/20 600/114 |
| 2002/0087049 A1 * | 7/2002 | Brock | A61B 34/20 600/114 |
| 2002/0087148 A1 * | 7/2002 | Brock | B25J 3/04 606/1 |
| 2002/0087166 A1 * | 7/2002 | Brock | A61B 17/0469 606/130 |
| 2002/0087169 A1 * | 7/2002 | Brock | A61B 17/10 606/139 |
| 2003/0078465 A1 * | 4/2003 | Pai | A61B 17/00234 600/16 |
| 2003/0097082 A1 * | 5/2003 | Purdy | A61B 17/12136 600/594 |
| 2003/0216710 A1 | 11/2003 | Hurt | |
| 2004/0054322 A1 * | 3/2004 | Vargas | A61M 25/00 604/95.04 |
| 2004/0122467 A1 * | 6/2004 | VanTassel | A61B 17/12122 606/200 |
| 2005/0159697 A1 * | 7/2005 | Dextradeur | A61M 25/0662 604/8 |
| 2006/0189975 A1 * | 8/2006 | Whayne | A61B 18/1492 606/41 |
| 2006/0211979 A1 * | 9/2006 | Smith | A61B 18/1492 604/11 |
| 2008/0091170 A1 * | 4/2008 | Vargas | A61M 25/0021 604/528 |
| 2008/0172037 A1 * | 7/2008 | Huang | A61M 25/0043 604/526 |
| 2008/0249458 A1 * | 10/2008 | Yamasaki | A61F 2/94 604/8 |
| 2008/0262406 A1 * | 10/2008 | Wiener | A61M 25/04 604/8 |
| 2009/0182268 A1 * | 7/2009 | Thielen | A61M 25/0138 604/95.04 |
| 2011/0282149 A1 * | 11/2011 | Vargas | A61M 25/0021 600/114 |

FOREIGN PATENT DOCUMENTS

| JP | 2001137346 A | 5/2001 |
|---|---|---|
| JP | 2007301363 A | 11/2007 |

OTHER PUBLICATIONS

CODMAN® Slim-line Aneurysm Clip System brochure; 2002; Codman and Shurtleff, Inc. Raynham, MA.

Japanese Patent Application No. 2013-107836 — Notification of Reasons of Refusal dated Dec. 28, 2017.

* cited by examiner

CATHETER CURVATURE BRACES AND METHODS OF USING SAME

BACKGROUND OF THE INVENTION

1. Field of the Invention

The invention relates to a device and methods for ensuring proper curvature for a catheter placed in a patient and more particularly to an implantable catheter having a curved elastic brace.

2. Description of the Related Art

There are a number of conditions in patients for which it is desirable to add or withdraw fluid. Some fluid management conditions involve the mammalian brain. Within the cranium, gray and white matter is suspended in cerebrospinal fluid and nourished by blood delivered through cerebral arteries. The gray matter has closely spaced cell bodies of neurons, such as in the cerebral cortex, and the underlying white matter contains densely packed axons that transmit signals to other neurons. Human brain tissue has different densities and comprises approximately eighty percent of the intracranial content, with blood and cerebrospinal fluid each normally comprising approximately ten percent.

Cerebrospinal fluid is produced by choroid plexus in several connected chambers known as ventricles and typically is renewed four to five times per day. Cerebrospinal fluid in a healthy human flows slowly and continuously through the ventricles, propelled by pulsations of the cerebral arteries. The fluid flows around the brain tissues and the spinal column, and then through small openings into the arachnoid membrane, which is the middle layer of the meninges surrounding the brain parenchyma and ventricles, where the fluid is finally reabsorbed into the bloodstream.

Under normal conditions, bodily mechanisms compensate for a change in fluid volume within the cranium through tissue resilience and by adjusting the total volume of blood and cerebrospinal fluid so that a small increase in fluid volume does not increase intracranial pressure. Similarly, a healthy brain compensates for an increase in intracranial pressure to minimize a corresponding increase in intracranial volume. This volume- and pressure-relationship can be explained in terms of cerebral compliance, which term is intended to include herein the terms elastance and intracranial compliance.

The brain is compliant as long as a person's auto-regulatory mechanism can compensate for any change in volume. As soon as the brain's auto-regulation or compensatory mechanisms fail, blood and cerebrospinal fluid cannot be displaced, and the brain can no longer adapt to any increase in fluid volume. A reduction in cerebral compliance eventually will lead to an undesired increase in intracranial pressure, also known as hydrocephalus. As more fluid volume is added, a threshold is reached beyond which small increases in volume lead to dramatic and unhealthy increases in intracranial pressure.

A typical device to treat fluid conditions such as hydrocephalus is a ventricular catheter disclosed by Watson et al. in U.S. Pat. No. 5,738,666. In one embodiment, ventricular catheter 22 has a plurality of fluid management openings, referred to as fluid flow apertures 56, near a distal tip 58 having a slit 60. The "distal" tip is the end farthest from a surgeon during implantation of the catheter. A terminal end 40 of a rigid introducer cannula 34 is inserted through the slit 60 during final placement of the ventricular catheter. A Tuohy-Borst adaptor 32 is secured to the proximal end of the introducer cannula 34. During set-up, a fiber-optic shaft 66 of an endoscope is advanced through the adaptor 32 and the cannula 34 until a fiber-optic terminal end 28 emerges past ventricular catheter terminal end 58 and aligns with introducer terminal end 40. Fiber-optic shaft 66 is then interlocked relative to introducer cannula 34. The aligned tips of the fiber-optic shaft 66 and the introducer cannula are then retracted proximally within catheter 22 during advancement through tissue until a selected ventricle is reached.

Unfortunately, complications associated with the ingrowth of choroid plexus into implanted ventricular catheters, also known as ventricular shunts, are common. The most common cause of ventricular shunt malfunction during treatment of hydrocephalus is occlusion, sometimes referred to as proximal shunt occlusion, with the fluid management openings frequently blocked by choroid plexus and/or brain parenchyma. Accurate placement of the catheter depends on both proper insertion trajectory and proper catheter tip positioning vis-a-vis ventricular configuration. Surgeons often attempt to place the distal tip of the ventricular catheter in front of the foramen of Monro to avoid the choroid plexus. However, creating a direct path to the front region restricts the surgical approaches to the ventricle. Theories on how the approaches differ based on seizure risk, choroid plexus obstruction, size and shape of target ventricular chamber and incidence of infection remain controversial.

Pre-curved catheters have been utilized for a variety of applications, typically where larger outer diameters are tolerated. U.S. Pat. No. 3,867,945 by Wendell Long discloses a Foley urethral catheter with a stylet that is semi-rigid and sufficiently stiff with an optimal curvature to guide the catheter during insertion.

Reinforced retention structures having an elastic member are disclosed by Teague et al. in U.S. Pat. No. 6,569,150. The retention structure provides an anchoring geometry to retain a catheter in position within the body of a patient, such as within a kidney and ureter.

It is therefore desirable to have a more versatile device and technique for positioning a catheter to manage bodily fluids, especially cerebrospinal fluid. A device is needed that minimizes obstruction and failure of a shunt system by facilitating the final catheter position within a ventricle of a brain, particularly when a more challenging occipital approach is utilized.

SUMMARY OF THE INVENTION

An object of the present invention is to enable a distal portion of a fluid management catheter to be positioned as desired within a patient.

Another object of the present invention is to minimize exposure of the distal portion of the catheter to tissue, such as choroid plexus, which may obscure openings in the catheter.

Yet another object of the invention is to optimize the trajectory and final position of shunt catheters, particularly in children with small or slit ventricles.

A still further object is to reduce the need for repair and/or replacement of implanted catheters.

This invention features a catheter curvature brace that is attachable to a distal portion of a shaft of a catheter and has an elongated frame with a distal end and a proximal end. The frame is formed with at least one curve in a relaxed curved configuration. At least two coupling elements are connected to the frame, each coupling element configured to engage an outer surface of the catheter. At least the frame is formed of an elastic, biocompatible material capable of being straightened by a force and then returning to the relaxed curved configuration after the force is removed, thereby bending the catheter to substantially conform to the relaxed curved configuration. The term "distal" refers to the end that is farthest from a surgeon or other user during implantation, while "proximal" refers to the end that is closest to the user.

In a preferred embodiment, the elastic, biocompatible material is a nitinol alloy. In some embodiments, at least one of the coupling elements is a ring and, in other embodiments, at least one of the coupling elements is a C-type member. In certain embodiments, at least one of the coupling elements is formed as a continuation of the frame.

In some embodiments, there are at least first and second catheter curvature braces, with the curvature of the second brace being different from that of the first brace.

This invention may be expressed as a fluid management catheter assembly suitable for implantation into the ventricle of a brain of a patient, including a catheter with an elongated shaft having a distal end and a proximal end, the shaft defining at least one lumen extending substantially therethrough, the shaft further defining a plurality of fluid management openings along a distal portion of the shaft, with the fluid management openings being in fluid communication with the lumen. The assembly further includes a catheter curvature brace attached to the distal portion of the shaft, the brace having an elongated frame with a distal end and a proximal end, the frame being formed with at least one curve in a relaxed curved configuration, and at least two coupling elements connected to the frame, each coupling element configured to engage an outer surface of the catheter. At least the frame is formed of an elastic, biocompatible material capable of being straightened by a force and then returning to the relaxed curved configuration after the force is removed, thereby bending the catheter to substantially conform to the relaxed curved configuration.

This invention may be still further expressed as a fluid management kit having a catheter as described above together with at least first and second catheter curvature braces. At least one curve of the second catheter brace differs from at least one curve of the first catheter brace.

This invention may also be expressed as a method for managing fluid within a patient, including selecting a catheter with an elongated shaft having a distal end and a proximal end. The shaft defines at least one lumen extending substantially therethrough. The shaft further defines a plurality of fluid management openings along a distal portion of the shaft, the fluid management openings being in fluid communication with the lumen. The method further includes selecting a catheter curvature brace attachable to the distal portion of the shaft, the brace having an elongated frame with a distal end and a proximal end, the frame being formed with at least one curve in a desired relaxed curved configuration, at least two coupling elements connected to the frame, each coupling element configured to engage an outer surface of the catheter, and at least the frame being formed of an elastic, biocompatible material capable of being straightened by a force and then returning to the desired relaxed curved configuration after the force is removed. The catheter brace is attached to the distal portion of the catheter to form a catheter assembly, a stylet is placed within the catheter lumen to apply the force to straighten the catheter assembly, and the catheter assembly is inserted within the patient at a targeted location, such as a ventricle of the brain of the patient. The stylet is then removed to allow the distal portion of the catheter to substantially conform to the desired relaxed curved configuration.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a catheter curvature brace that is attachable to a distal portion of a shaft of a catheter and has an elongated frame with a distal end and a proximal end. The frame is formed with at least one curve in a relaxed curved configuration. At least two coupling elements are connected to the frame, each coupling element configured to engage an outer surface of the catheter. At least the frame is formed of an elastic, biocompatible material capable of being straightened by a force and then returning to the relaxed curved configuration after the force is removed, thereby bending the catheter to substantially conform to the relaxed curved configuration.

Figure 1:
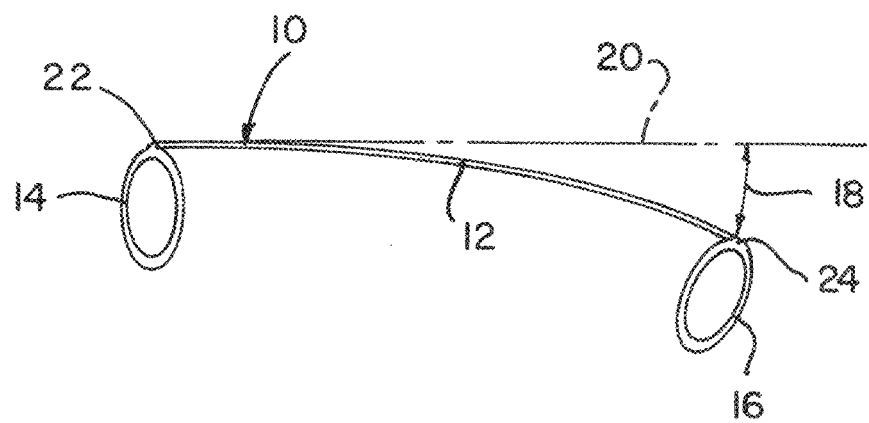
FIG. 1 is a schematic side view of a first catheter curvature brace according to the present invention.
Figure 2:
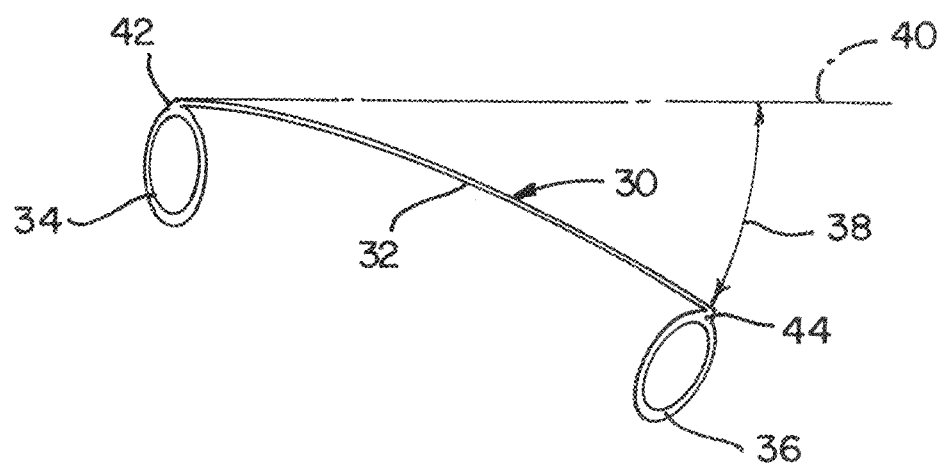
FIG. 2 is a schematic side view of a second catheter curvature brace according to the present invention having a different curvature than the brace of FIG. 1.

FIG. 1 shows a first curvature brace 10 having a frame 12 and ring-shaped coupling elements 14 and 16. Frame 12 has a proximal end 22, a distal end 24, and is formed in a first curve at an angle, represented by arrow 18 relative to longitudinal axis 20 of proximal end 22, of approximately twenty degrees in this construction. Similarly, FIG. 2 shows a second curvature brace 30 having a frame 32 and ring-shaped coupling elements 34 and 36. Frame 32 has a proximal end 42, a distal end 44, and is formed in a second curve at an angle, represented by arrow 38 relative to longitudinal axis 40 of proximal end 42, of approximately thirty degrees in this construction.

Figure 3:
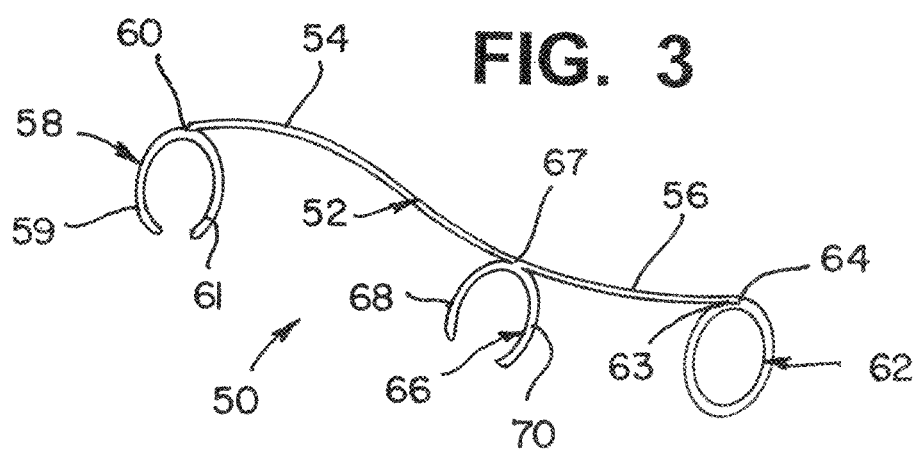
FIG. 3 is a schematic side view of yet another catheter curvature brace according to the present invention having a complex curvature.

A third curvature brace 50 is shown in FIG. 3 having a frame 52 formed in a relaxed complex curvature having a plurality of curves 54 and 56. In some constructions, frame 52 has multiple curves along a single plane and, in other constructions, has multi-planar curves. A first, C-shaped coupling element 58, having curved legs 59 and 61, is connected to frame 52 at proximal end 60, a second, ring-shaped coupling element 62 is connected to frame 52 at distal end 64, and a third, C-shaped coupling element 66, having curved legs 68 and 70, is connected to frame 52 at an intermediate position 67.

In preferred constructions, at least frames 12, 32 and 52 are formed of a super-elastic material such as a nitinol alloy or super-elastic polymers. Various suitable super-elastic materials are described in U.S. Pat. No. 6,569,150 by Teague et al., for example. Known techniques can be utilized to impart desired curvatures, such as heating the elastic material to a sufficiently high temperature and then bending the material into the desired shapes.

Figure 4:
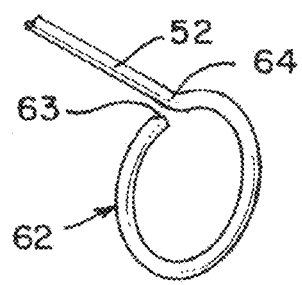
FIG. 4 is an enlarged view of the distal end of the brace of FIG. 3.

One or more of the coupling elements 14, 16, 34, 36, 58, 62 and 66 are formed of the same material as the corresponding frames 12, 32 and 52 in some constructions and are formed of different materials in other constructions. When the coupling elements are ring-shaped, such as illustrated for coupling elements 14, 16, 34, 36 and 62, it is preferable to form them as a continuation of material forming corresponding frames 12, 32 and 52, respectively. One ring-shaped configuration is illustrated in FIG. 4 for coupling element 62, wherein nitinol wire forming frame 52 and coupling element 62 terminates in an end 63 that is not physically connected to distal end 64 of frame 52. Coupling element 62 may also be said to have an open-ring shape. Otherwise, open- or closed-ring-shaped material can be attached by brazing or other suitable biocompatible attachment technique. Similarly, legs 59, 61, 68 and 70 are attached as individual legs in some constructions and as paired, continuous legs in other constructions.

Figure 5:
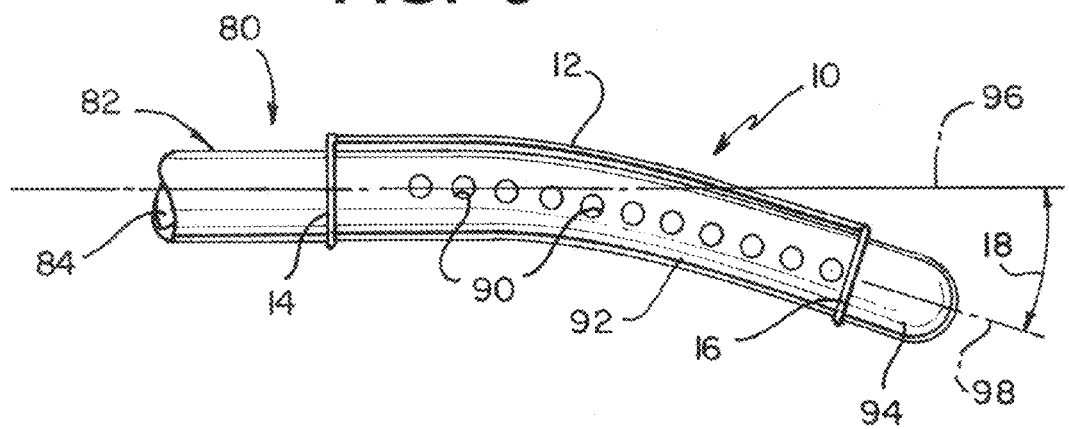
FIGS. 5 and 6 are schematic side views of the brace of FIG. 1 attached to a ventricular catheter to form a catheter assembly, with the assembly further including a stylet in FIG. 6 which forces the assembly to a straightened condition.
Figure 6:
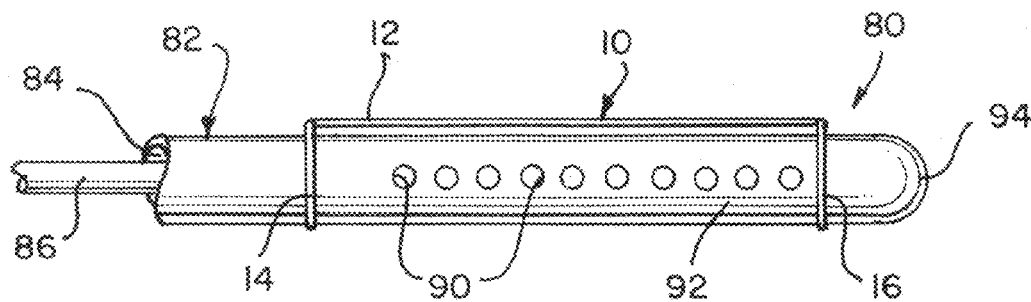

Catheter curvature brace 10, FIG. 1, is shown mated with a ventricular catheter 82 in FIGS. 5 and 6 to form a catheter assembly 80. Catheter 82 has at least one lumen 84 in which a stylet 86 is insertable as illustrated in FIG. 6 to force catheter assembly 80 to match the orientation of stylet 86, which is straight in this construction. A plurality of fluid management openings 90 are formed in a distal portion 92 which terminates in a distal tip 94. Suitable ventricular catheters and stylets are commercially available from Codman & Shurtleff of Raynham, Mass., for example.

Catheter assembly 80 returns to the relaxed curved configuration shown in FIGS. 1 and 5 after force is discontinued, such as by removing stylet 86. In other words, distal portion 92 returns substantially to the angle represented by arrow 18, shown in FIG. 5 relative to the longitudinal axis 96 of catheter 82 and axis 98 of the center of distal tip 94. Brace 10 is typically placed on the "outside" of a desired curve, with coupling elements positioned along catheter 82 to minimize blockage of openings 90.

In one assembly technique, a surgeon or other healthcare professional selects an appropriate fluid management catheter and selects a curvature brace according to the present invention having a desired relaxed curved configuration for a particular fluid management procedure for a patient. In addition to having a desired curvature, the brace is also selected to have a plurality of coupling elements which are appropriately sized for the outer diameter of the selected catheter. The professional then forces the distal tip of the catheter through the coupling elements by squeezing or stretching the catheter. In one technique according to the present invention, a ventricular catheter is introduced through the coupling elements by pushing the catheter through the coupling elements utilizing a rigid stylet. A sleeve, pliers or other tool can be utilized to assist in the assembly process. A spreading device may be utilized to temporarily widen an open-ring-shaped coupling element such as shown in FIG. 4 or a C-shaped coupling element as illustrated in FIG. 3.

Figure 7:
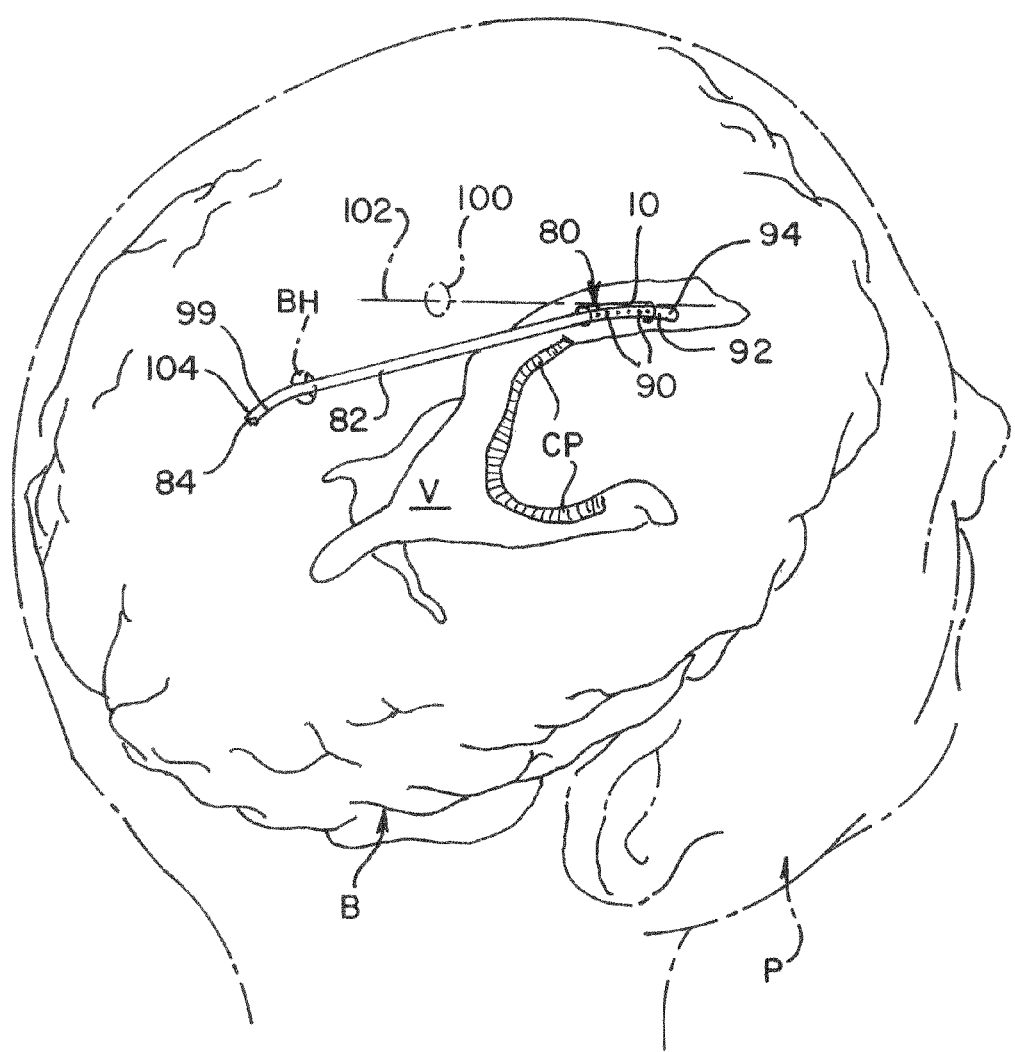
FIG. 7 is an upper, partial cross-sectional view of a patient's head showing the ventricular catheter assembly of FIG. 5 after implantation within a ventricle of the brain.

FIG. 7 illustrates catheter assembly 80 after placement through burr hole BH and through tissue of brain B of a patient P. Distal portion 92 is shown positioned within a ventricle V. Brace 10 bends and holds distal portion 92 in a desired curved configuration after a stylet, endoscope or other delivery device, utilized in a conventional manner to place catheter assembly 80, has been removed from lumen 84. Proximal end 99 of catheter 82 typically remains outside of the skull of patient P to be connected to a pump or other fluid management device. Preferably, an orientation mark 104, such as a groove, contrasting color dot or stripe, and/or darker material, indicates the rotational position of brace 10 relative to mark 104.

Dashed circle 100, FIG. 7, represents a more forward location of a burr hole needed for conventional catheter placement along substantially straight trajectory 102 to achieve the alignment axis 98 of distal tip 94, such as illustrated in FIG. 5. However, such a conventional placement of a conventional catheter itself would not achieve a curved configuration as accomplished by the present invention to ideally match the curvature of the ventricle V, FIG. 7, and maintain fluid management openings 90 away from the choroid plexus CP lining portions of the ventricle.

Thus, while there have been shown, described, and pointed out fundamental novel features of the invention as applied to preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A fluid management catheter assembly suitable for implantation into a ventricle in a brain of a patient, comprising:
   a catheter with an elongated shaft having a distal end and a proximal end, the shaft defining at least one lumen extending substantially therethrough, the shaft further defining a plurality of fluid management openings along a distal portion of the shaft, the fluid management openings being in fluid communication with the lumen; and
   a catheter curvature brace attached to the distal portion of the shaft, the brace having an elongated frame with a distal end and a proximal end, the frame being formed with at least one pre-defined curve in a relaxed curved configuration, and at least two coupling elements connected to the frame, each coupling element configured to engage an outer surface of the catheter; and
   at least the frame being formed of an elastic, biocompatible material capable of being straightened by a force and then returning to the pre-defined relaxed curved configuration after the force is removed, thereby bending the catheter to substantially conform to the pre-defined relaxed curved configuration.

2. The catheter brace of claim 1 wherein the elastic, biocompatible material is a nitinol alloy.

3. The catheter brace of claim 1 wherein at least one of the coupling elements is formed as a substantially circular ring.

4. The catheter brace of claim 1 wherein at least one of the coupling elements is formed as a continuation of the frame.

5. A fluid management kit, comprising:
   a catheter with an elongated shaft having a distal end and a proximal end, the shaft defining at least one lumen extending substantially therethrough, the shaft further defining a plurality of fluid management openings along a distal portion of the shaft, the fluid management openings being in fluid communication with the lumen; and at least first and second catheter curvature braces attachable to the distal portion of the shaft, each brace having an elongated frame with a distal end and a proximal end, the frame being formed with at least one pre-defined curve in a relaxed curved configuration, at least two coupling elements connected to the frame, each coupling element configured to engage an outer surface of the catheter, and at least the frame being formed of an elastic, biocompatible material capable of being straightened by a force and then returning to the pre-defined relaxed curved configuration after the force is removed, thereby bending the catheter to substantially conform to the pre-defined relaxed curved configuration; and wherein the at least one curve of the first catheter brace is different from the at least one curve of the second brace.

6. The catheter brace of claim 5 wherein the elastic, biocompatible material is a nitinol alloy.

7. The catheter brace of claim 5 wherein at least one of the coupling elements is formed as a substantially circular ring.

* * * * *